United States Patent
Beyer et al.

(10) Patent No.: US 6,730,326 B2
(45) Date of Patent: May 4, 2004

(54) THERMODYNAMICALLY STABLE MODIFICATION OF 1-(4-CARBAZOLYL-OXY-3[2-(2-METHOXYPHENOXY)-ETHYLAMINO]-2-PROPANOL PROCESS FOR ITS PREPARATION AND PHARMACEUTICAL COMPOSITIONS CONTAINING IT

(75) Inventors: Peter Beyer, Neustadt (DE); Erhard Reinholz, Heddesheim (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 10/166,188

(22) Filed: Jun. 10, 2002

(65) Prior Publication Data

US 2003/0036559 A1 Feb. 20, 2003

Related U.S. Application Data

(63) Continuation of application No. 09/463,346, filed as application No. PCT/EP98/04475 on Jul. 18, 1998, now abandoned.

(30) Foreign Application Priority Data

Jul. 22, 1997 (EP) .............................. 97112491

(51) Int. Cl.$^7$ .................... A61K 9/16; C07D 209/82
(52) U.S. Cl. ...................... 424/489; 548/444
(58) Field of Search ............... 424/489; 548/444

(56) References Cited

U.S. PATENT DOCUMENTS

| | | | |
|---|---|---|---|
| 4,503,067 A | | 3/1985 | Wiedemann et al. |
| 4,697,022 A | * | 9/1987 | Leinert ................. 548/444 |

FOREIGN PATENT DOCUMENTS

| | | |
|---|---|---|
| DE | 28 12 926 | 10/1979 |
| DE | 2815926 | 10/1979 |
| EP | 4920 | 10/1979 |
| EP | 0 127 099 | 12/1984 |
| EP | 127099 | 12/1984 |
| HU | 193011 | 8/1987 |

OTHER PUBLICATIONS

Feuerstein et al., *Carvediol Update III: Rationale for use in Congestive Heart Failure*, Drugs Today, vol. 31F, pp. 1–23 (1995).
Derwent Abstract for EP 127099.

* cited by examiner

Primary Examiner—Thurman K. Page
Assistant Examiner—Amy E Pulliam
(74) Attorney, Agent, or Firm—George W. Johnston; Patricia S. Rocha-Tramaloni; Bernard Lau

(57) ABSTRACT

The present invention provides a thermodynamically stable modification of (±)1-(4-carbazolyloxy)-3-[2-(2-methoxyphenoxy)ethylamino]-2-propanole and pharmacologically acceptable salts or optically active forms thereof as well as processes for their preparation and pharmaceutical compositions containing one or more of them.

1 Claim, 6 Drawing Sheets

Figure 1:
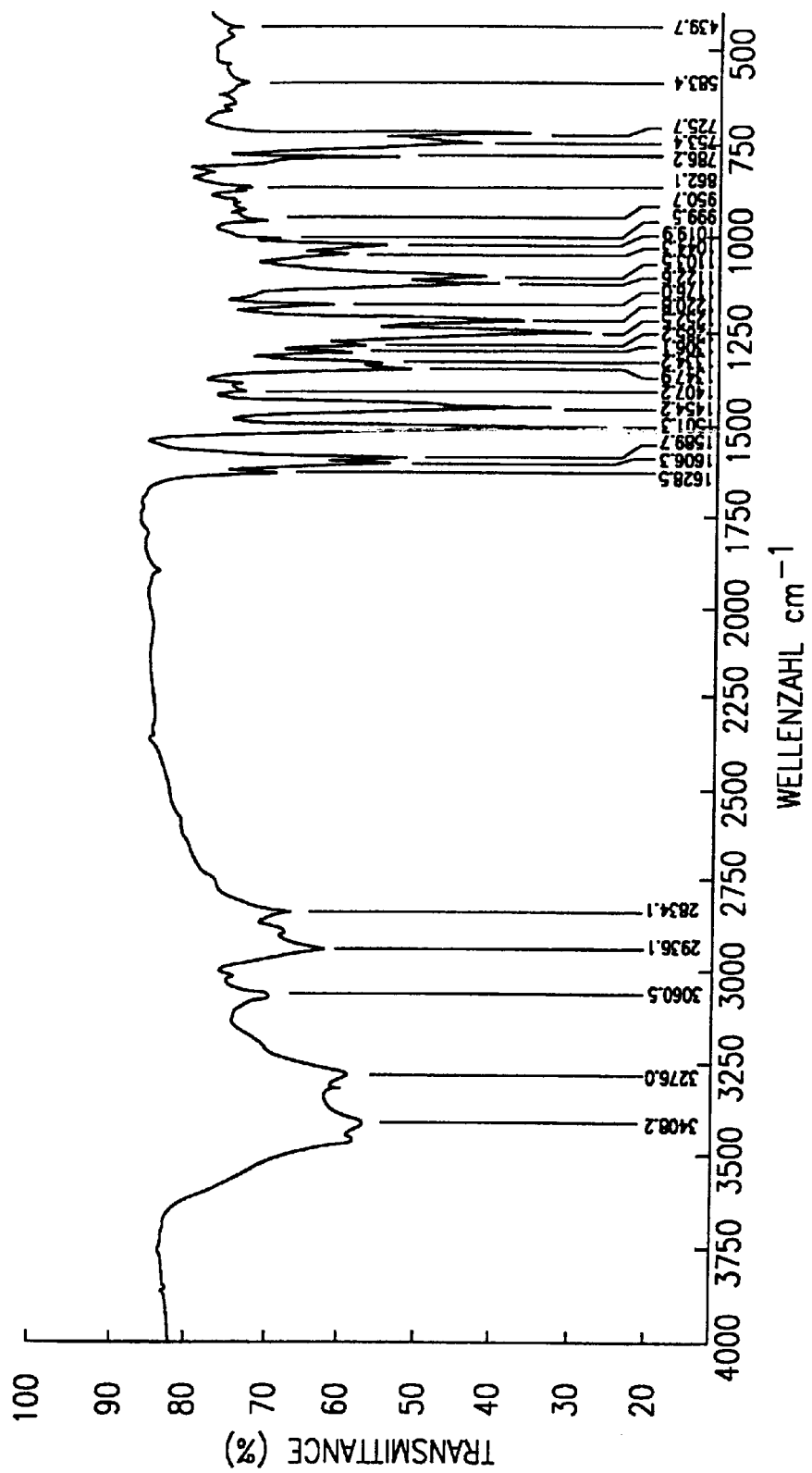

THERMODYNAMICALLY STABLE MODIFICATION OF 1-(4-CARBAZOLYL-OXY-3[2-(2-METHOXYPHENOXY)-ETHYLAMINO]-2-PROPANOL PROCESS FOR ITS PREPARATION AND PHARMACEUTICAL COMPOSITIONS CONTAINING IT

RELATION BACK UNDER 35 U.S.C. § 120

This is a continuation of application Ser. No. 09/463,346 filed on Jan. 21, 2000 now abandoned, which is a 371 of PCT/EP98/04475, filed Jul. 18, 1998.

SUMMARY OF THE INVENTION

The present invention relates to a new thermodynamically stable modification of (±)1-(4-carbazolyloxy)-3-[2-(2-methoxyphenoxy)ethylamno]-2-propanole (Carvedilol), pharmacologically acceptable salts or optically active forms thereof, processes for the preparation, and pharmaceutical compositions containing it.

BACKGROUND OF THE INVENTION

Carvedilol, having a melting point of 114–115° C. is a compound with excellent pharmacological properties (Merck Index 11. Ed. No. 1882), known to be active in the treatment of cardiac diseases. The preparation and its use in medicine is described in EP-B-0 004 920.

Carvedilol has a chiral center and, as such, can exist either as individual stereoisomers or in racemic form. Both the racemate and stereoisomers may be obtained according to procedures well known in the art (EP-B-0127099).

It has now been discovered that Carvedilol can be isolated in two different modifications depending upon the method of preparation which are distinguishable by their infra-red Raman and X-ray powder diffraction spectra, and their melting points. The two polymorphic forms are monotropic and they are hereinafter designated as Form I and Form II. It is desirable to prepare a therapeutic agent consisting of an unique and defined composition which has a high storage stability.

DETAILED DESCRIPTION OF THE INVENTION

The present invention provides a thermodynamically stable crystalline form of Carvedilol substantially free of other physical forms having a melting point about 123–126° C., and an infra-red spectrum with a sharp peak at 3451 $cm^{-1}$, which is referred to hereinafter as Form I.

The invention also provides a process for producing this substantially pure Form I. In another embodiment of this invention, there is provided a pharmaceutical formulation containing the substantially pure Form I of Carvedilol as an active ingredient.

Finally, the present invention provides a method of using the new substantially pure form to prevent and/or treat circulatory and cardiac diseases.

Where reference is made in this application to Form I or Form II substantially free of other physical forms, it preferably means that at least 90% by weight of Form I or Form II is present in that modification.

Form II is the modification of Carvedilol prepared and purified according to EP-B-0 004 920.

Surprisingly it was now found that a new thermodynamically stable modification of Carvedilol (Form I) with a higher melting point is obtained when the process of manufacture is slightly altered.

The melting points of each Forms I respectively II depend upon their level of purity, consequently Form I has been found to have a melting point of about 123–126° C. Form II about 114–115° C.

Furtheron it has been discovered that Form I is that of being the thermodynamically stable form, which is of advantage. Therefore this thermodynamically stable form is given preference in the preparation of pharmaceutical formulations.

Pharmaceutically acceptable salts are considered to be encompassed within the compounds and the method of the present invention. The term "pharmaceutically acceptable salts" refers to salts of substantially pure Form I which are substantially non-toxic to living organism. For the conversion of Carvedilol into its pharmacologically acceptable salts, it is reacted, preferably in an organic solvent, with an equivalent amount of an inorganic or organic acid, for example hydrochloric acid, hydrobromic acid, phosphoric acid, sulphuric acid, acetic acid, citric acid, maleic acid or benzoic acid. It should be recognized that any particular anion forming a part of any salt of this invention is not critical, so long as the salt, as a whole, is pharmacologically acceptable and as long as the anion moiety does not contribute undesired qualities.

For the resolution of the racemates, there can be used for example, tartaric acid, malic acid, camphoric acid or camphorsulphonic acid.

According to another aspect, the invention provides a pharmaceutical composition, which comprises Form I substantially free of other physical forms and a pharmaceutical acceptable carrier or adjuvant.

The compounds of the present invention may be administered by any suitable route, preferably in the form of a pharmaceutical composition adapted to such a route and in dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising Carvedilol of Form I of the present invention, in association with one or more non-toxic pharmaceutically acceptable carriers and/or adjuvants (collectively referred to herein as "carrier materials") and, if desired, other active ingredients. The compounds and compositions may, for example, be administered orally, intravascularly, intraperitoneally, subcutaneously, intramuscularly or topically.

For all administrations, the pharmaceutical composition may be in the form of for example, a tablet, capsule, creme, ointment, gel, lotion, suspension or liquid. The pharmaceutical composition is preferably made in the form of a dosage unit containing a particular amount of the active ingredient. Examples of such dosage units are tablets or capsules. A suitable daily dose for a mammal may vary widely depending on the condition of the patient and other factors. However, a dose from about 0.01 to 100 mg/kg body weight, particularly from about 0.05 to 3 mg/kg body weight, respectively 0.01–10 $mg/cm^2$ skin, may be appropriate. The active ingredient may also be administered by injection.

The dose regimen for treating a disease condition with the compounds and/or compositions of this invention is selected in accordance with a variety of factors, including the type, age, weight, sex and medical conditions of the patient and in accordance to the severity of the desease and thus may vary widely.

For therapeutic purposes, the compounds of the invention are ordinarily combined with one ore more adjuvants appropriate to the indicated route of administration. If per os, the compound may be admixed with lactose, sucrose, starch powder, cellulose esters of alkanoic acids, cellulose alkyl ester, talc, stearic acid, magnesium stearat, magnesium oxide, sodium and calcium salts of phosphoric and sulphuric acids, gelatine, acacia, sodium alginate, polyvinyl-pyrrolidone and/or polyvinyl alcohol, and thus tabletted or encapsulated for convenient administration. Alternatively, the compound may be dissolved in water, polyethylene glycol, propylene glycol, ethanol, corn oil, cotton seed oil, peanut oil, sesam oil, benzyl alcohol, sodium chloride and/or various buffers. Appropriate additives for the use as ointments, cremes or gels are for example paraffine, vaseline, natural waxes, starch cellulose, or polyethyleng-lycole. Other adjuvants and modes of administration are well and widely known in the pharmaceutical art.

Appropriate dosages in any given instance, of course, depend upon the nature and severity of the condition treated, the route of administration and the species of mammal involved, including its size and any individual idiosyncracies.

Representative carriers, dilutions and adjuvants include, for example, water, lactose, gelatine starch, magnesium stearate, talc, vegetable oils, gums, polyalkylene glycols, petroleum gelly, etc. The pharmaceutical compositions may be made up in a solid form, such as granules, powders or suppositories, or in liquid form, such as solutions, suspensions or emulsions. The pharmaceutical compositions may be subjected to conventional pharmaceutical adjuvants, such as preservatives, stabilizers, wetting agents, emulsifiers, buffers, etc.

As indicated, the dose administered and the treatment regimen will be dependent, for example, on the disease, the severity thereof, on the patient being treated and his response to treatment and, therefore, may be widely varied.

Characterization of Forms I and II of Carvedilol

Thermomicroscopy

Thermal analysis was carried out with a Kofler heating stage (Reichert, Vienna) mounted on a video-equipped Olympus microscope BH-2 or with a Kofler heating stage microscope Thermovat® (Reichert, Vienna); both microscopes with polarisation facility and digital thermometer.

Form II consists of heterogeneously looking rhombohe-dral to hexagonally shaped lamellar crystals up to a size of 120 μm, which melt about 114–115° C. whereas Form I consists of 40 μm large grains, respectively prisms, which melt about 123–126° C.

Differential Scanning Calorimetry (DSC)

DSC was carried out with DSC-7 (Perkin-Elmer, Norwalk, Conn. USA) equipped with cooling system CCA-7, perforated Al sample capsules (25 μl), weighed object 1.5 mg each (ultra-micro weighing scale UM 3, Mettler, CH-Greifensee, Switzerland). Nitrogen 4.0 as flushing gas (20 ml min$^{-1}$). Computer-aided recording of DSC signal. Calibration of temperature indication for CCA curves with melting point for water and caffeine anhydrate (melting point 236.2° C.), each with tightly sealed sample capsule. Calibration of ordinates (DSC signal) with melting heat of indium 99.999% (Perkin-Elmer, Norwalk, Conn., USA).

The measured melting points correspond to the ones determined thermomicroscopically. It could be estimated by the way of the measured melting heats (Form I: $\Delta H_f$ 48.2 kJ/mol: Form II $\Delta H_f$ 51.0 kJ/mot), that the crystallisate consisting of Form I is contaminated with approximately 2 to 3% of Form II, which could also be seen thermomicro-scopically.

FT-IR, FT Raman Spectroscopy and X-Ray Diffractometry

FT-IR spectroscopy was carried out with a Bruker IFS 25 FT-IR spectrometer. For the production of the KBr compacts approximately 1 mg of sample was powdered with 270 mg of KBr. The spectra were recorded in transmission mode ranging from 4000 to 600 cm$^{-1}$. Resolution: 2 cm$^{-1}$ (50 interferograms).

FT Raman spectroscopy was carried out with Bruker RFS 100 FT Raman spectrometer, equipped with a diode-pumped Nd:YAG laser (1064 nm) and a liquid nitrogen cooled highly sensitive detector. The powdered samples were pressed into small aluminium fittings, the spectra were recorded at an initial capacity of 200 mW, resolution: 4 cm$^{-1}$ (50 interferograms).

X-ray powder diffractometry was carried out with a Simens X-ray diffractometer D-5000. Diffrac/AT with θ/θ goniometer, Cu$_{K\alpha}$-rays, nickel filter for monochromatisation, rotation of sample during measurement, scintillation counter, angular range 2° to 40° (2θ), steps of 0.01° (2θ), measuring time 2 secs.

Figure 2:
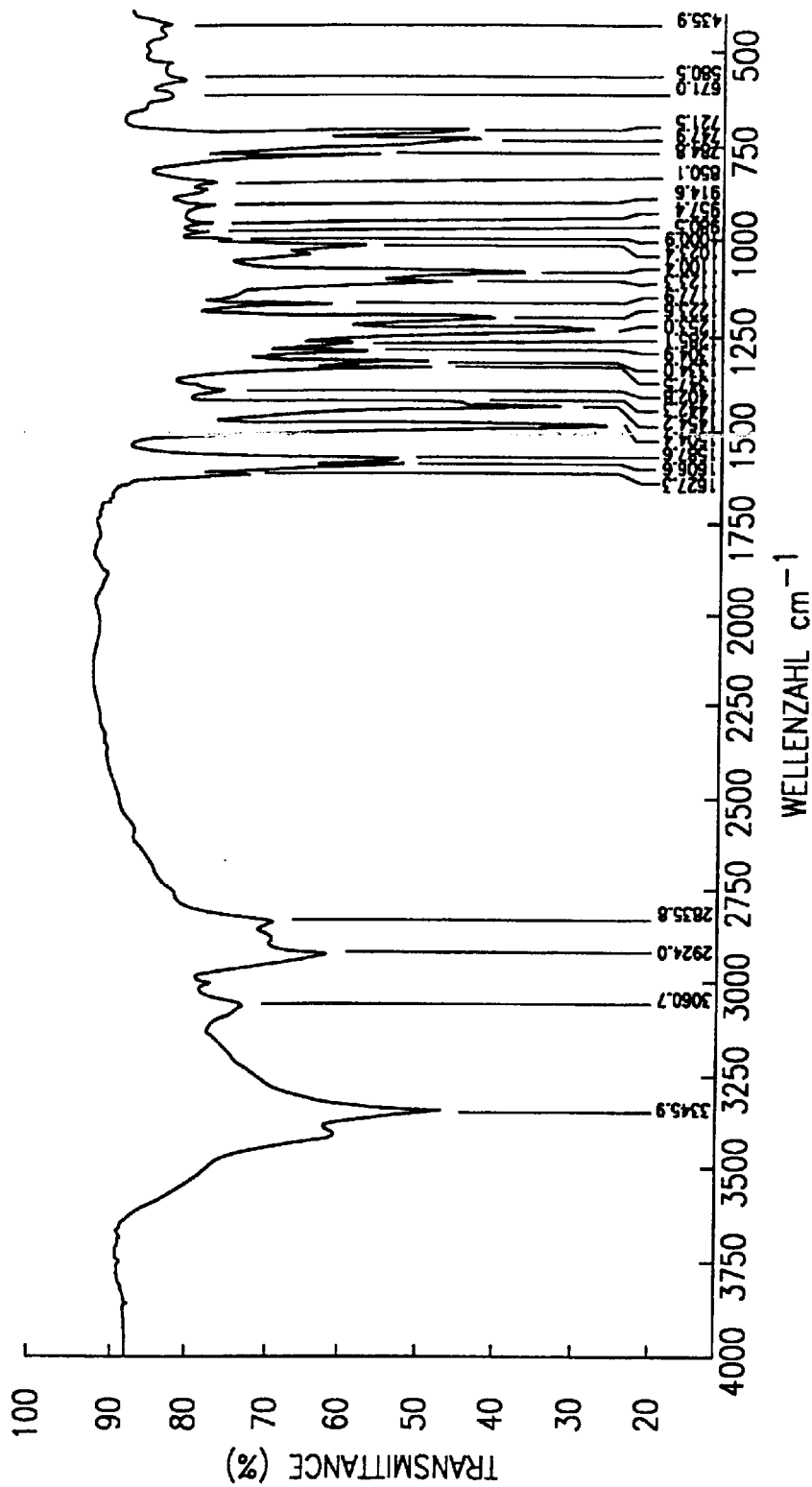
Figure 3:
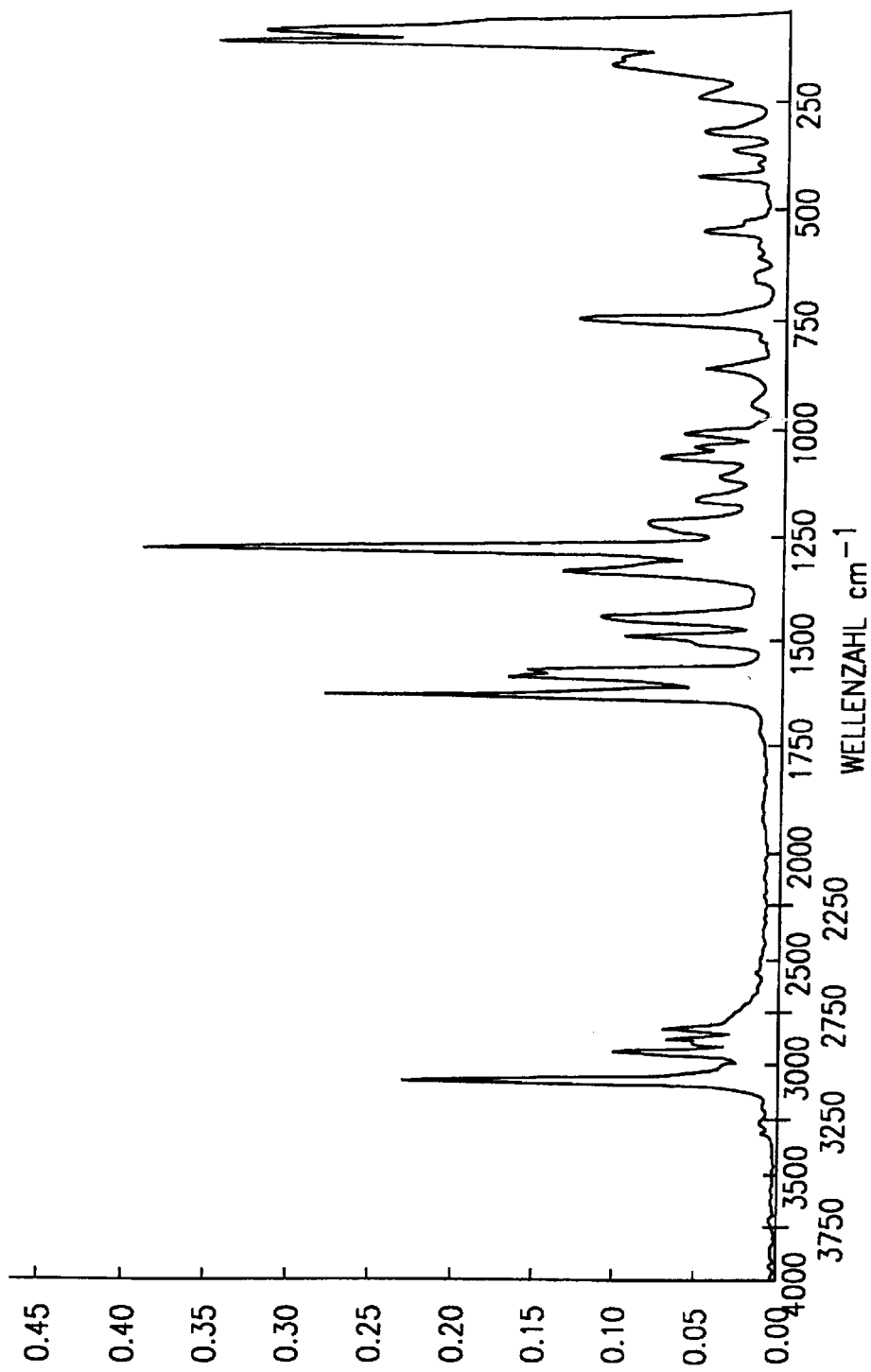
Figure 4:
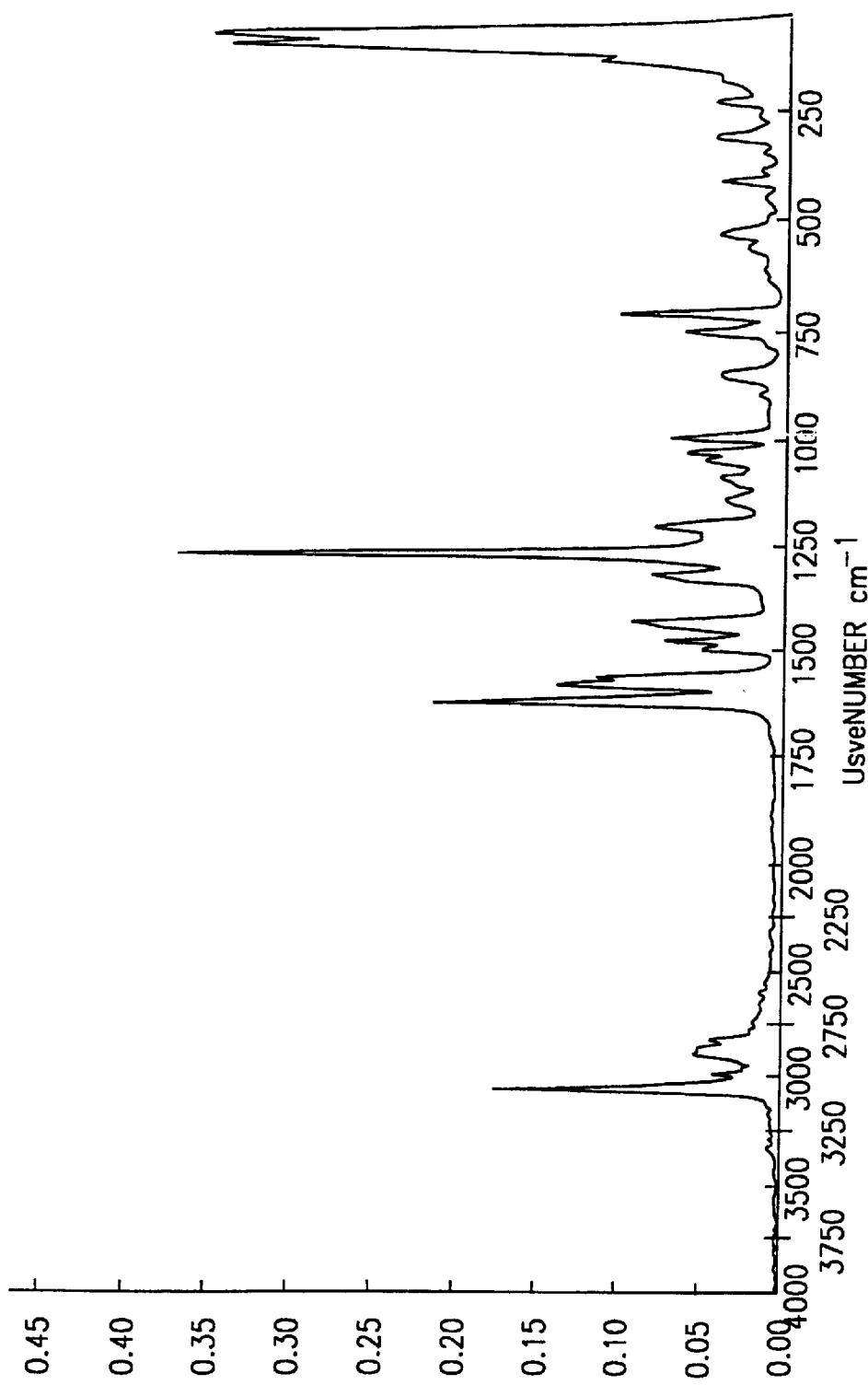
Figure 5:
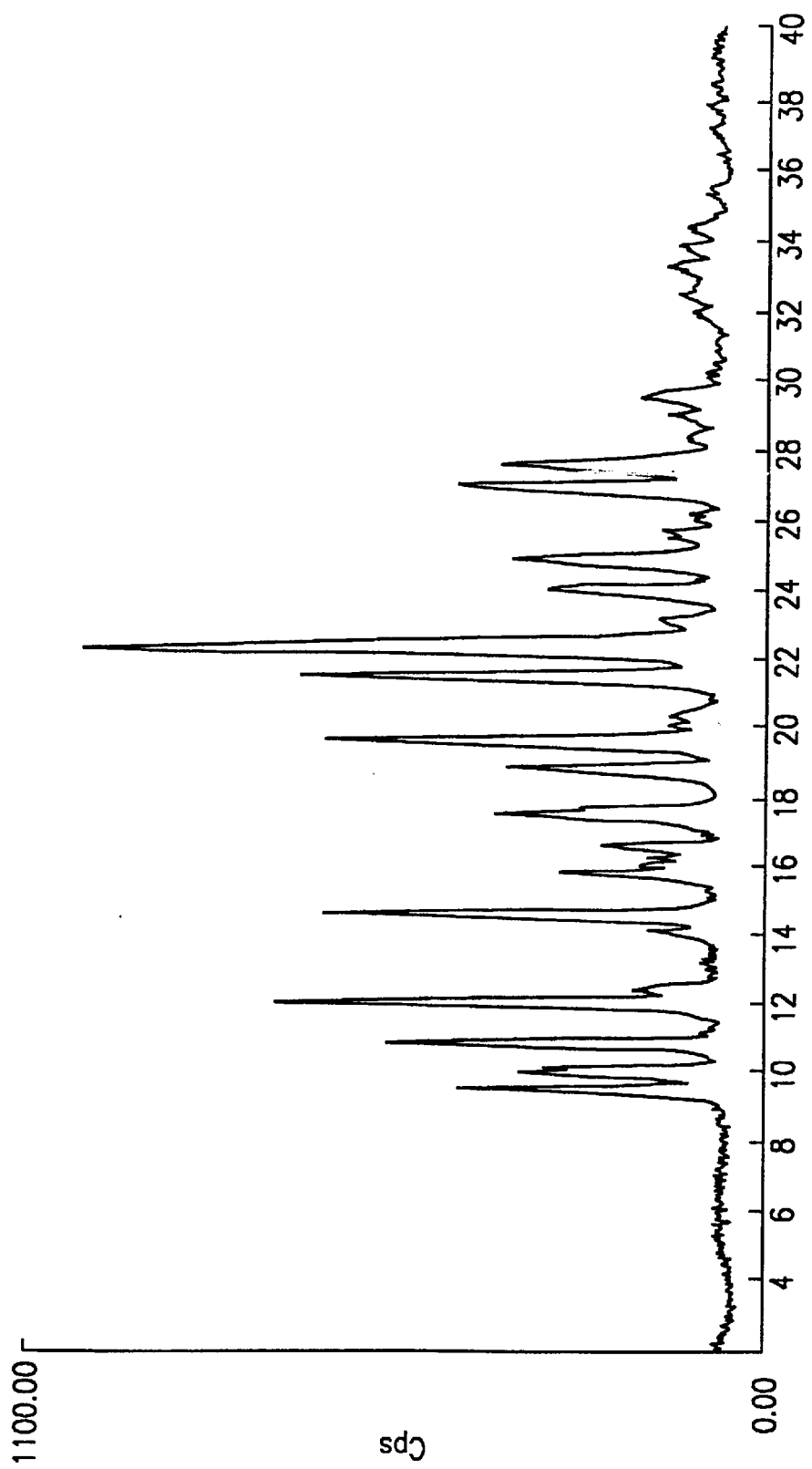
Figure 6:
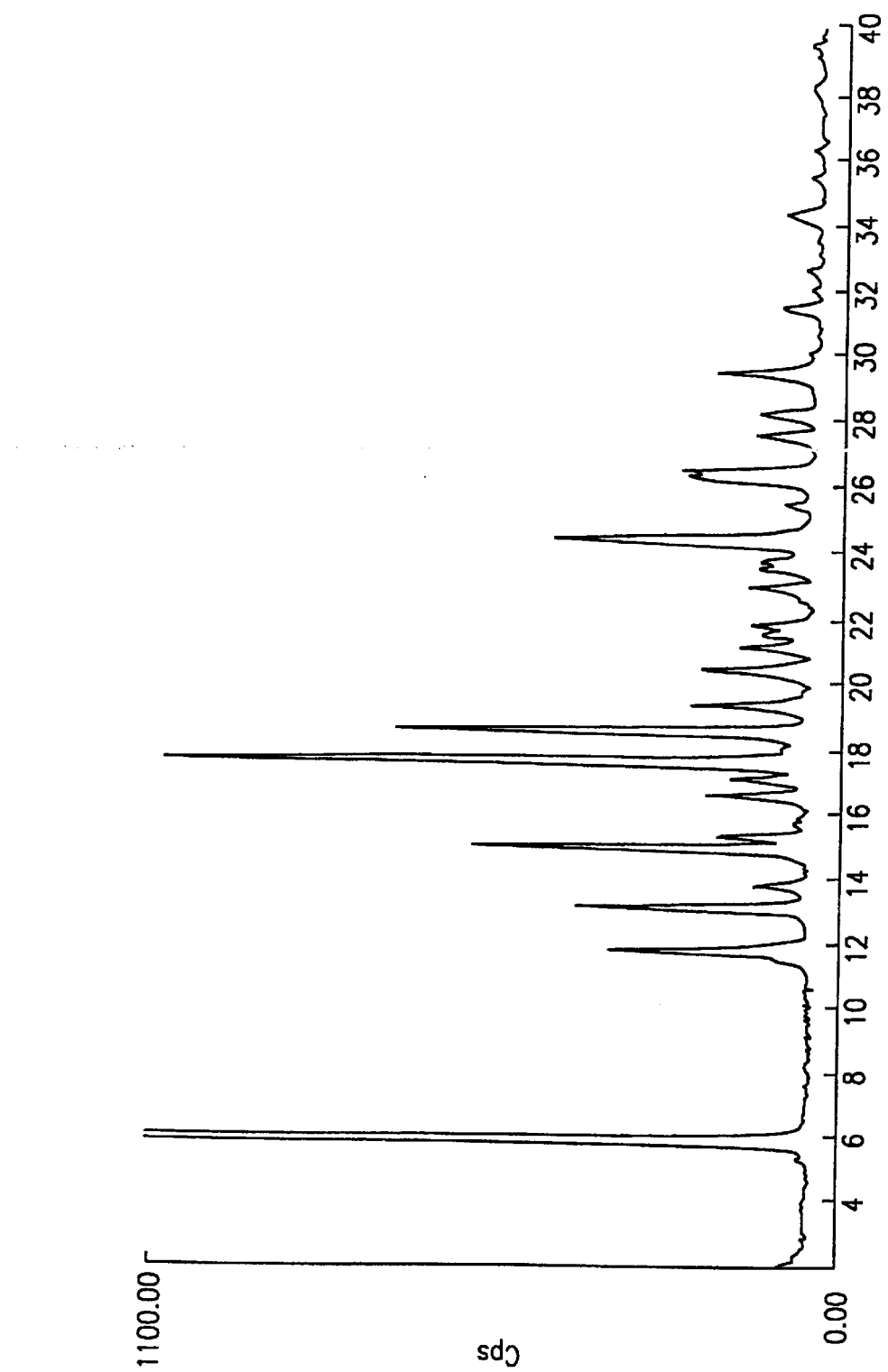

The IR spectra of both modifications show great differences in the stretching vibration range (Form I 3451 cm$^{-1}$, Form II 3345 cm$^{-1}$)(FIGS. 1,2), which are caused by different hydrogen bridges. This corresponds to the Raman spectra differing only little. The biggest difference in the Raman spectra is at approximately 2942 and approximately 755 cm$^{-1}$ (FIGS. 3,4). The X-ray powder diffraction pattern of Form I has characteristic peaks occuring at 2θ=9.5, 10.8, 12.0, 14.6, 19.6, 21.5, and 22.3 (FIG. 5) whereas the characteristic peaks of Form II occur at 2θ=5.9, 14.9, 17.6, 18.5, and 24.4 (FIG. 6).

Process for Preparing Form I Carvedilol

EXAMPLE 1

Crude Carvedilol is prepared according to the procedure described in EP-B-0 004 920, in methanol. Crude Carvedilol (based on 300 g dry Carvedilol), 15 g CXA-coal and 2800 ml methanol are heated for 15 minutes under reflux in a three-neck-flask. The hot solution is filtered and washed with 300 ml hot methanol and heated under reflux again. Subsequently the solution is cooled down during half an hour to 30° C. stirred between 3 to 22 hours and cooled down slowly to 0° C. in 3½ hours. After stirring the solution for additional two hours at 0° C. the product is isolated, washed three times with 40 ml methanol and dried under vacuo at 60° C. for 24 hours. 203–255 g of pure Form I are obtained and characterized as described before.

Form II can be obtained by an additional recrystallization process in isopropanol.

EXAMPLE 2

A 1:1 mixture of Form I and Form II was suspended in isopropanol and agitated with a magnetic stirrer for 18 h in a tightly sealed glass cylindar. During this time the temperature was repeatedly increased and lowered between 10 and 25° C. Subsequently the sample was filtered with a micro glass filter funnel (G3), dried and evacuated. The IR spectrum of this sample corresponds to Form I: The DSC curve does not show a peak between 114–115° C. thus this is pure Form I.

It will be understood that the specification and examples are illustrative but not limitative of the present invention and that other embodiments within the spirit and scope of the invention will suggest themselves to those skilled in the art.

What is claimed is:

1. A crystalline form of (±)1-(4-carbazolyloxy)-3-[2-(2-methoxyphenoxy)ethylamino]-2-propanole substantially free of other forms, having a melting point of about 123–126° C., the following X-ray diffraction pattern obtained from a $CU_{ka}$ radiation at $2\theta=9.5, 10.8, 12.0, 14.5, 19.6, 21.5, 22.3$, and an infrared spectrum with a sharp peak at $3451$ $cm^{-1}$, or a pharmaceutically acceptable salt or optically active form thereof.

* * * * *